(12) United States Patent
Ren et al.

(10) Patent No.: US 8,962,880 B2
(45) Date of Patent: Feb. 24, 2015

(54) AMORPHOUS ASIATIC TROMETHAMINE SALT AND PREPARATION METHOD THEREOF

(75) Inventors: Guobin Ren, Shanghai (CN); Ying Liu, Shanghai (CN); Jinyao Chen, Shanghai (CN); Xiaoling Huang, Shanghai (CN); Lin Xiao, Shanghai (CN); Li Cai, Shanghai (CN); Zhen Zhang, Shanghai (CN); Xuejun Wu, Shanghai (CN); Haiyan Sun, Shanghai (CN); Quanhai Liu, Shanghai (CN); Liling Jin, Shanghai (CN); Minyu Liu, Shanghai (CN); Yifang Deng, Shanghai (CN); Zhiru Xu, Shanghai (CN); Renhai Chen, Shanghai (CN); Chungang Li, Shanghai (CN); Xiangduan Tan, Shanghai (CN); Yan Qin, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 0 days.

(21) Appl. No.: 14/006,198

(22) PCT Filed: Mar. 21, 2012

(86) PCT No.: PCT/CN2012/072690
§ 371 (c)(1),
(2), (4) Date: Oct. 24, 2013

(87) PCT Pub. No.: WO2012/126363
PCT Pub. Date: Sep. 27, 2012

(65) Prior Publication Data
US 2014/0243553 A1    Aug. 28, 2014

(30) Foreign Application Priority Data
Mar. 22, 2011    (CN) .......................... 2011 1 0069862

(51) Int. Cl.
*C07C 227/14*    (2006.01)
*C07C 215/10*    (2006.01)
*C07C 229/38*    (2006.01)
*C07J 63/00*    (2006.01)

(52) U.S. Cl.
CPC ............. *C07C 227/14* (2013.01); *C07C 215/10* (2013.01); *C07C 229/38* (2013.01); *C07J 63/008* (2013.01)
USPC ......................................................... 562/510

(58) Field of Classification Search
USPC .................................................. 562/508, 510
See application file for complete search history.

(56) References Cited

U.S. PATENT DOCUMENTS 3,366,669 A    1/1968    Ratsimamanga
8,742,167 B2 *    6/2014    Liu et al. ....................... 562/510

FOREIGN PATENT DOCUMENTS

| CN | A-1347398 | 5/2002 |
| CN | A-101969942 | 2/2011 |
| EP | 12760240.7 | 10/2013 |
| WO | WO 00/63148 | 10/2000 |
| WO | WO 2009/089365 A2 | 7/2009 |

OTHER PUBLICATIONS

International Search Report dated Jun. 28, 2012 issued in International Patent Application No. PCT/CN2012/072690 (with English Translation).
Written Opinion of the International Searching Authority dated Jun. 28, 2012 issued in International Patent Application No. PCT/CN2012/072690 (with English Translation).
Aug. 20, 2014 Office Action issued in Chinese Patent Application No. 201110069862.6 w/translation.

* cited by examiner

*Primary Examiner* — Shailendra Kumar
(74) *Attorney, Agent, or Firm* — Oliff PLC

(57) ABSTRACT

An amorphous asiatic tromethamine salt and the preparation method thereof. The method includes the steps of: (1) dissolving asiatic acid in an organic solvent; step (2) mixing with tromethamine; step (3) stirring and salifying the same, and then removing the organic solvent. The method for preparing the amorphous asiatic tromethamine salt is easy and effective, and the water solubility and bioavailability of the asiatic tromethamine salt thus obtained are greatly compared with the prior art.

12 Claims, 2 Drawing Sheets

AMORPHOUS ASIATIC TROMETHAMINE SALT AND PREPARATION METHOD THEREOF

This application is a 371 of PCT/CN2012/072690, filed Mar. 21, 2012.

TECHNICAL FIELD

The present invention relates to an amorphous asiatic tromethamine salt and its preparation method.

BACKGROUND ART

Asiatic acid (2α,3β,23-trihydroxy-ursa-12-en-28-oic acid), was first extracted from *Centella asiatica* by Bontems et al. The pharmacologic effects of asiatic acid are quite wide. It can be used to treat burn, chronic ulcers, or skin deformity associated with tuberculosis or leprosy. It also owns a certain curative effect on cardiovascular disease, hepatotoxicity and so on. Moreover, some study discloses that asiatic acid has an effect on anti-depression, anti-fibrosis, antibiosis, antineoplastic, anti-oxidation, etc.

Although there exists four hydrophilic groups (3 hydroxyl groups and 1 carboxyl group) in the molecular structure, the wettability of asiatic acid is relatively poor, and it is practically insoluble in water. Physicochemical properties require a particular process method and excipient in the formulation of preparations for topic use, especially hydrophilic use. In addition, it is known that the cutaneous absorption primarily proceeds transepidermally (intra- and trans-cellular) and it is mainly controlled by the effect of effective components on the cuticle that mainly consists of keratin and water. Therefore, besides the formulation problem, a proper bioavailability of asiatic acid at an epidermis level remains to be realized.

Salts of asiatic acid are protonated salts formed by asiatic acid and pharmaceutically acceptable alkali. The water solubility of salts of asiatic acid is better than that of asiatic acid, which makes the development of salts of asiatic acid quite significant.

The salts of asiatic acid with hemi-succinate, salts of hemi-succinate, as well as with alkylaminoalkanols and dialkylaminoalkanols have been reported currently by U.S. Pat. No. 3,366,669. CN 1238330C disclosed salts of asiatic acid with ethylenediamine, ethanolamine, diethanolamine, lysine, benzyltrimethylammonium hydroxide, and tetramethylammonium hydroxide etc. WO 2009/089365 disclosed the ammonium salt, sodium salt, potassium salt, sodium carbonate salt, sodium phosphate salt, amino triacetate salt, and trometamol salt of asiatic acid.

The compounds aforementioned all can be used to prepare the aqueous solution for topic pharmaceutical use.

The solubility of the known free acid of asiatic acid, trometamol salt of asiatic acid reported in WO 2009/089365 and other salts of asiatic acid is all unsatisfactory. How to prepare a kind of trometamol salt of asiatic acid with much higher solubility as well as good bioavailability is always the research issue for the scientists at present.

CONTENTS OF THE INVENTION

The technical problem to be solved by the present invention is that to overcome the defeat that it is hard to promote the solubility and bioavailability of the known free acid and trometamol salt of asiatic acid at the same time, a kind of amorphous asiatic tromethamine salt and its preparation method are provided. The present invention found a new path to prepare the amorphous asiatic acid, and this preparation method is simple and effective. The asiatic acid trometamol salt given by this method has a much higher solubility and bioavailability than that given by the prior art has, which widens the application range of this salt and endows this salt with a wide range of application prospect.

The present invention provides an amorphous asiatic tromethamine salt.

Wherein, the amorphous asiatic tromethamine salt can preferably be prepared by the following method: step (1) a solution of asiatic acid is prepared by dissolving asiatic acid in an organic solvent; step (2) the said solution is mixed with tromethamine; step (3) salt forming reaction is carried out under stirring, and the organic solvent is removed.

Wherein, the molar ratio between the asiatic acid and tromethamine can be selected according to the routine method in this field, and generally tromethamine is over-dose. Preferably, the molar ratio between the asiatic acid and the tromethamine is 0.8:1~1:1.5.

In step (1), the organic solvent can be selected from the routine organic solvent in this field that can dissolve asiatic acid, preferably is selected form alcohols solvent, more preferably is one or more selected from the group consisting of saturated monohydric alcohols with 1-5 carbon(s) and aromatic alcohols with 7-8 carbons, most preferably is one or more selected from the group consisting of methanol, anhydrous ethanol, isopropanol, n-butyl alcohol, n-amyl alcohol, benzyl alcohol and n-propanol, the best is one or more selected from the group consisting of methanol, anhydrous ethanol and isopropanol.

In step (1), preferably the dissolution accompanies with heating, and the heat temperature is commonly the reflux temperature of the organic solvent.

In step (1), the amount of the organic solvent can be selected according to the routine method of this reaction in this field, preferably make the asiatic acid dissolved, commonly is 50~150 ml/g asiatic acid.

In step (2), the mixing temperature is preferably 50~100° C.

In step (3), the temperature of salt forming reaction can be selected according to the routine method of this reaction in this field, preferably is 50~100° C. The time of salt forming reaction can be selected according to the routine method of this reaction in this field, preferably is 0.5~9 h.

In step (3), the method for removal the organic solvent is the routine method for removal the organic solvent in this field, commonly is evaporation under the pressure of 0.05 MP~0.1 MP, for example rotary evaporation. The temperature of evaporation is preferably 50~100° C.

Preferably, after step (3), drying is carried out. The drying can be carried out according to the routine method in this field, such as ambient drying or vacuum drying. The temperature of drying is preferably 50~80° C.

The present invention also provide a preparation method of amorphous asiatic tromethamine salt, wherein the amorphous asiatic tromethamine salt can be preferably prepared by the following method: step (1) a solution of asiatic acid is prepared by dissolving asiatic acid in an organic solvent; step (2) the said solution is mixed with tromethamine; step (3) salt forming reaction is carried out under stirring, and the organic solvent is removed.

Wherein, the molar ratio between the asiatic acid and the tromethamine can be selected according to the routine method in this field, and generally tromethamine is over-dose. Preferably, the molar ratio between the asiatic acid and the tromethamine is 0.8:1~1:1.5.

In step (1), the organic solvent can be selected from the routine organic solvent in this field that can dissolve asiatic acid, preferably is selected from alcohols solvent, more preferably is one or more selected form the group consisting of saturated monohydric alcohols with 1-5 carbon(s) and aromatic alcohols with 7-8 carbons, most preferably is one or more selected form the group consisting of methanol, anhydrous ethanol, isopropanol, n-butyl alcohol, n-amyl alcohol, benzyl alcohol and n-propanol, the best is one or more selected form the group consisting of methanol, anhydrous ethanol and isopropanol.

In step (1), preferably the dissolution accompanies with heating, which makes the asiatic acid totally dissolved, and the heat temperature is commonly the reflux temperature of the organic solvent.

In step (1), the amount of the organic solvent can be selected according to the routine method of this reaction in this field, preferably make the asiatic acid dissolved, commonly is 50~150 ml/g asiatic acid.

In step (2), the mixing temperature is preferably 50~100° C.

In step (3), the temperature of salt forming reaction can be selected according to the routine method of this reaction in this field, preferably is 50~100° C. The time of salt forming reaction can be selected according to the routine method of this reaction in this field, usually determined by when the reaction system becomes clear, preferably is 0.5~9 h.

In step (3), the method for removal the organic solvent is the routine method for removal the organic solvent in this field, commonly is evaporation under the pressure of 0.05 MP~0.1 MP. The temperature of evaporation is preferably 50~100° C.

Preferably, after step (3), drying is carried out. The drying can be carried out according to the routine method in this field, such as ambient drying or vacuum drying. The temperature of drying is preferably 50~80° C.

In the present invention, any of the preferable conditions aforementioned can be combined with other preferable ones so long as this combination conforms to the common sense in this field, and through this combination, the preferable technical solution of the present invention is obtained.

The raw materials and reagents used in the present invention are all commercial available.

The effective results of the present invention is that the present invention obtains amorphous asiatic tromethamine salt by a simple method, which possesses a higher solubility and bioavailability than the crystalline one does and has a wider range of application prospect.

EMBODIMENTS

Figure 1:
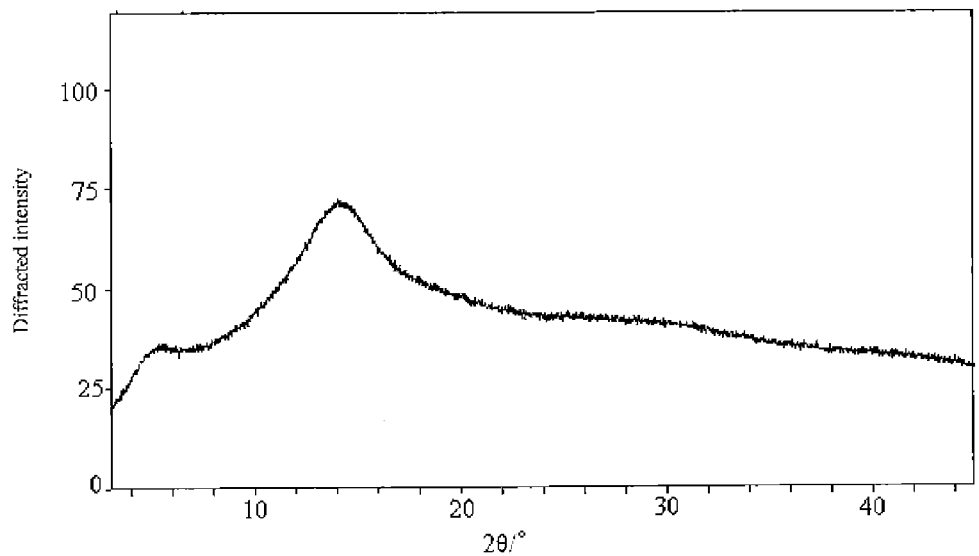
FIG. 1 shows PXRD (Powder X Ray Diffraction) of amorphous asiatic tromethamine salt.

Examples are used to further illustrate the present invention. However, the present invention shouldn't be limited by these examples. The raw materials used in the examples are all products which can be purchased.

Example 1

Mix 1 g (2.046 mmol) asiatic acid with 100 ml anhydrous ethanol at room temperature, and heat the solution up to reflux temperature. When the acid being dissolved completely in ethanol, add 0.31 g (2.559 mmol) tromethamine into the solution and keep stirring for 0.5 h to give a clear solution. Then, evaporate the solvent at 60° C. under vacuum, dry the product in a vacuum drying oven at 50° C. to give the amorphous asiatic tromethamine salt.

Example 2

Mix 1 g (2.046 mmol) asiatic acid with 100 ml methanol at room temperature, and heat the solution up to 50° C. When the acid being dissolved completely in methanol, add 0.35 g (2.889 mmol) tromethamine into the solution and keep stirring for 3 h to give a clear solution. Then, evaporate the solvent at 50° C. under ambient pressure, dry the product in a vacuum drying oven at 50° C. to give the amorphous asiatic tromethamine salt.

Example 3

Mix 1 g (2.046 mmol) asiatic acid with 150 ml isopropanol at room temperature, and heat the solution up to 70° C. When the acid being dissolved completely in isopropanol, add 0.37 g (3.054 mmol) tromethamine into the solution and keep stirring for 8 h to give a clear solution. Then, evaporate the solvent at 70° C. with a vacuum degree of 0.05 MP, dry the product in a vacuum drying oven at 80° C. to give the amorphous asiatic tromethamine salt.

Example 4

Mix 1 g (2.046 mmol) asiatic acid with 150 ml n-butyl alcohol, and heat the solution up to 100° C. When the acid being dissolved completely in n-butyl alcohol, add 0.35 g (2.889 mmol) tromethamine into the solution and keep stirring for 3 h to give a clear solution. Then, evaporate the solvent at 100° C. with a vacuum degree of 0.03 MP, dry the product in a vacuum drying oven at 70° C. to give the amorphous asiatic tromethamine salt.

Example 5

Mix 1 g (2.046 mmol) asiatic acid with the blend of 50 ml isopropanol and 50 ml methanol, and heat the solution up to 50° C. When the acid being dissolved completely, add 0.37 g (3.054 mmol) tromethamine into the solution and keep stirring for 9 h to give a clear solution. Then, evaporate the solvent at 70° C. with a vacuum degree of 0.04 MP, dry the product in a vacuum drying oven at 60° C. to give the amorphous asiatic tromethamine salt.

Example 6

Mix 1 g (2.046 mmol) asiatic acid with the blend of 100 ml methanol and 50 ml ethanol, and heat the solution up to 60° C. When the acid being dissolved completely, add 0.31 g (2.559 mmol) tromethamine into the solution and keep stirring for 2 h to give a clear solution. Then, evaporate the solvent at 60° C. under vacuum, dry the product in a vacuum drying oven at 50° C. to give the amorphous asiatic tromethamine salt.

Example 7

Mix 1 g (2.046 mmol) asiatic acid with 100 ml n-amyl alcohol, and heat the solution up to 100° C. When the acid being dissolved completely, add 0.31 g (2.559 mmol) tromethamine into the solution and keep stirring for 2 h to give a clear solution. Then, evaporate the solvent at 100° C. under vacuum, dry the product in a vacuum drying oven at 50° C. to give the amorphous asiatic tromethamine salt. Examples for indicating the effective results The preparation method of comparative sample: the product described in WO 2009/089365, as the comparative sample of the present invention, was prepared according to the method disclosed by WO 2009/089365.

1. XRD Analysis

Figure 2:
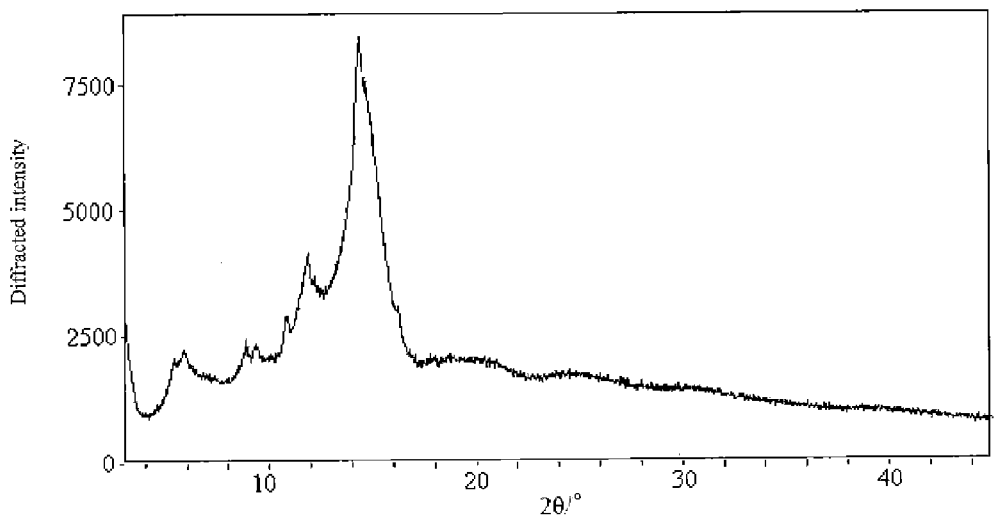
FIG. 2 shows PXRD of crystalline asiatic acid tromethamine salt reported by WO 2009/089365.

Amorphous asiatic tromethamine salt of examples 1-7 and comparative sample were analyzed by XRD respectively, and the results are shown in FIGS. 1 and 2. It can be known from FIG. 1 that there exists no sharp diffraction peak in the XRD spectrum, which shows the asiatic acid tromethamine salt of examples 1-7 are all amorphous. It can be known from FIG. 2 that the comparative sample is semi-crystalline, which is different from the amorphous one of the present invention.

2. Solubility Analysis

The analysis results of amorphous asiatic tromethamine salt of examples 1-7 and comparative sample are shown in table 1.

TABLE 1 the results of solubility analysis

| solute | solubility (mg/ml) |
| --- | --- |
| amorphous asiatic tromethamine salt in water | 0.64 |
| comparative sample in water | 0.21 |
| asiatic acid in water | 0.03 |
| amorphous asiatic tromethamine salt in methanol | 150.4 |
| comparative sample in methanol | 88.5 |
| asiatic acid in methanol | 33.1 |

Table 1 shows that the solubility of amorphous asiatic tromethamine salt (both in water and in alcohol) is higher than that of the semi-crystalline comparative sample on the whole.

3. Bioavailability Analysis

TABLE 2 formula

| formula: | dosage |
| --- | --- |
| asiatic acid tromethamine salt | 50 mg |
| microcrystalline cellulose | 150 mg |
| cross-linked polyvinylpyrrolidone | 14 mg |
| pregelatinized starch | 45 mg |
| magnesium stearate | 5 mg |

Figure 3:
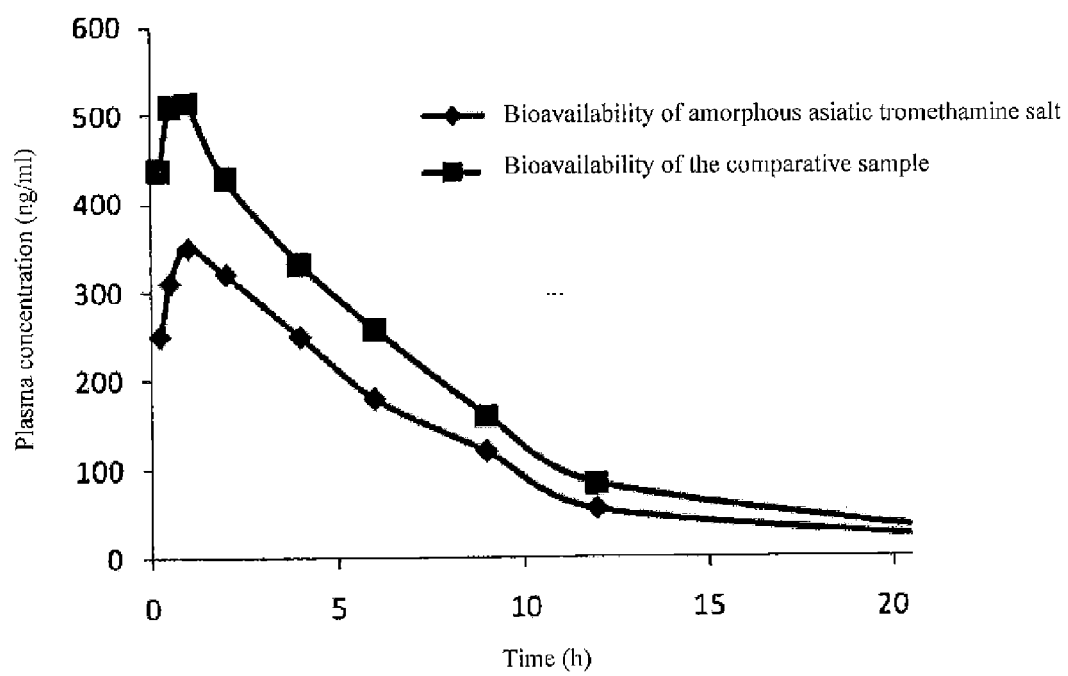
FIG. 3 shows the spectrum of bioavailability of amorphous and crystalline asiatic acid tromethamine salt.

Preparation Method of Test Samples:

Amorphous asiatic tromethamine salt, the comparative sample, microcrystalline cellulose and crosslinked polyvinylpyrrolidone were smashed and sifted. According to the formula of table 2, amorphous asiatic tromethamine salt and the comparative sample were respectively mixed with microcrystalline cellulose, cross-linked polyvinylpyrrolidone and pregelatinized starch, and then respectively mixed with 5% ethanol solution, pelletized, dried, further respectively mixed with magnesium stearate, and compressed to form tablets. Wherein, the screen mesh for sifting asiatic acid tromethamine salt is 60 meshes, for sifting microcrystalline cellulose and cross-linked polyvinylpyrrolidone is 80 meshes. The particle size, when pelletizing, is 20 meshes. The temperature of drying is preferably to control the moisture less than 3 wt % at 90° C. The bioavailability results of these samples are shown in FIG. 3. It can be seen from FIG. 3 that the bioavailability of the amorphous salt provided by the present invention (ca. 10.4%) is quite higher than that of the comparative sample (ca. 7.6%).

The invention claimed is:

1. An amorphous asiatic tromethamine salt.

2. The amorphous asiatic tromethamine salt as defined in claim 1, wherein the amorphous asiatic tromethamine salt is prepared by the following method:
   step (1): preparing a solution of asiatic acid by dissolving asiatic acid in an organic solvent;
   step (2): mixing the solution with tromethamine; and
   step (3): carrying out a salt forming reaction under stirring, and removing the organic solvent.

3. The amorphous asiatic tromethamine salt as defined in claim 2, wherein a molar ratio between the asiatic acid and the tromethamine is 0.8:1~1:1.5.

4. The amorphous asiatic tromethamine salt as defined in claim 2, wherein the organic solvent is an alcohol solvent.

5. The amorphous asiatic tromethamine salt as defined in claim 2, wherein in step (1), the dissolution of the asiatic acid in the organic solvent is accompanied by heating.

6. The amorphous asiatic tromethamine salt as defined in claim 2, wherein in step (2), the mixing is carried out a temperature of 50~100° C.

7. The amorphous asiatic tromethamine salt as defined in claim 2, wherein in step (3):
   the salt forming reaction is carried out at a temperature of 50~100° C. for 0.5~9 h, and
   the organic solvent is removed evaporation under a pressure of 0.05 MP~0.1 MP.

8. A preparation method of the amorphous asiatic tromethamine salt as defined in claim 1, comprising:
   step (1): preparing a solution of asiatic acid by dissolving asiatic acid in an organic solvent;
   step (2): mixing the solution with tromethamine;
   step (3): carrying out a salt forming reaction under stirring, and removing the organic solvent.

9. The preparation method as defined in claim 8, wherein one or more of the following conditions are satisfied:
   the organic solvent is an alcohol solvent; and
   the mixing is carried out at a temperature of 50~100° C.

10. The preparation method as defined in claim 8, wherein one or more of the following conditions are satisfied:
    a molar ratio between the asiatic acid and the tromethamine is 0.8:1~1:1.5;
    the dissolution of the asiatic acid in the organic solvent is accompanied by heating;
    the salt forming reaction is carried out at a temperature of 50~100° C. for 0.5~9 h; and
    the organic solvent is removed by evaporation under a pressure of 0.05 MP~0.1 MP.

11. The amorphous asiatic tromethamine salt as defined in claim 4, wherein the organic solvent is one or more alcohols selected from the group consisting of saturated monohydric alcohols with 1-5 carbon(s), and aromatic alcohols with 7-8 carbons.

12. The amorphous asiatic tromethamine salt as defined in claim 4, the organic solvent is one or more alcohols selected from the group consisting of methanol, anhydrous ethanol, isopropanol, n-butyl alcohol, n-amyl alcohol, benzyl alcohol and n-propanol.

* * * * *